US011737679B2

(12) United States Patent
Frushour et al.

(10) Patent No.: US 11,737,679 B2
(45) Date of Patent: Aug. 29, 2023

(54) LOCALIZATION SYSTEMS AND METHODS OF USE

(71) Applicant: Covidien LP, Mansfield, MA (US)

(72) Inventors: Scott E. M. Frushour, Boulder, CO (US); Evgeni Kopel, Barkan (IL)

(73) Assignee: Covidien LP, Mansfield, MA (US)

( * ) Notice: Subject to any disclaimer, the term of this patent is extended or adjusted under 35 U.S.C. 154(b) by 853 days.

(21) Appl. No.: 16/715,072

(22) Filed: Dec. 16, 2019

(65) Prior Publication Data

US 2020/0214769 A1 Jul. 9, 2020

Related U.S. Application Data

(60) Provisional application No. 62/800,665, filed on Feb. 4, 2019, provisional application No. 62/789,604, filed on Jan. 8, 2019.

(51) Int. Cl.
*A61B 5/06* (2006.01)
*A61B 34/20* (2016.01)
*A61B 18/14* (2006.01)
*A61B 90/00* (2016.01)
*A61B 18/00* (2006.01)

(52) U.S. Cl.
CPC .............. *A61B 5/062* (2013.01); *A61B 18/14* (2013.01); *A61B 34/20* (2016.02); *A61B 2018/00541* (2013.01); *A61B 2018/00595* (2013.01); *A61B 2034/2051* (2016.02); *A61B 2090/3958* (2016.02)

(58) Field of Classification Search
CPC .............................. A61B 5/05; A61B 2090/395
See application file for complete search history.

(56) References Cited

U.S. PATENT DOCUMENTS

| 5,242,456 A | 9/1993 | Nash et al. |
| 5,415,666 A | 5/1995 | Gourlay et al. |
| 5,509,923 A | 4/1996 | Middleman et al. |
| 5,512,037 A | 4/1996 | Russell et al. |
| 8,187,315 B1 | 5/2012 | Clauson et al. |
| 9,463,003 B2 | 10/2016 | Gordin et al. |
| 10,231,718 B2 | 3/2019 | Ciulla et al. |
| 10,342,540 B2 | 7/2019 | Smith et al. |

(Continued)

FOREIGN PATENT DOCUMENTS

| EP | 1598020 A1 | 11/2005 |
| EP | 2578167 A1 | 4/2013 |

(Continued)

OTHER PUBLICATIONS

International Search Report corresponding to the International Application No. PCT/US2017/014038, dated Apr. 5, 2017; 5 pages.

(Continued)

*Primary Examiner* — Angela M Hoffa
*Assistant Examiner* — Younhee Choi
(74) *Attorney, Agent, or Firm* — Carter, DeLuca & Farrell LLP

(57) ABSTRACT

A localization tool for localizing and marking a nodule of a patient includes a magnetic portion for locating a magnetic fiducial marker disposed in or adjacent the nodule, and an electrocautery element for marking the nodule or tissue adjacent the nodule upon locating the magnetic fiducial marker.

13 Claims, 3 Drawing Sheets

(56) References Cited

U.S. PATENT DOCUMENTS

| | | | |
|---|---|---|---|
| 10,537,316 B2 | 1/2020 | Smith et al. | |
| 2007/0265491 A1* | 11/2007 | Krag | A61B 34/74 600/37 |
| 2008/0221599 A1 | 9/2008 | Starksen | |
| 2012/0289776 A1 | 11/2012 | Keast et al. | |
| 2015/0051642 A1 | 2/2015 | Broom et al. | |
| 2015/0080714 A1* | 3/2015 | Dillard | A61N 1/406 600/424 |
| 2017/0035407 A1 | 2/2017 | Duan et al. | |
| 2017/0042610 A1* | 2/2017 | Smith | A61M 25/0113 |
| 2017/0095315 A1* | 4/2017 | van der Weide | A61B 90/98 |
| 2017/0209132 A1 | 7/2017 | Bhatt et al. | |
| 2017/0360465 A1* | 12/2017 | Smith | A61B 18/1442 |

FOREIGN PATENT DOCUMENTS

| | | |
|---|---|---|
| JP | 2004321482 A | 11/2004 |
| JP | 2005103107 A | 4/2005 |
| JP | 2008142516 A | 6/2008 |
| JP | 2008155006 A | 7/2008 |
| JP | 4320207 B2 | 8/2009 |
| JP | 4472680 B2 | 6/2010 |
| WO | 2009034922 A1 | 3/2009 |
| WO | 2012054845 A2 | 4/2012 |
| WO | 2014055193 A1 | 4/2014 |
| WO | 2018227592 A1 | 12/2018 |

OTHER PUBLICATIONS

Australian Examination Report issued in corresponding Australian Application No. 2017209092, dated Nov. 30, 2018; 5 pages.
International Search Report and Written Opinion of the International Searching Authority, dated Feb. 20, 2019, corresponding to counterpart International Application No. PCT/US2018/059867; 15 total pages.

* cited by examiner

LOCALIZATION SYSTEMS AND METHODS OF USE

CROSS-REFERENCE TO RELATED APPLICATIONS

This application claims the benefit of and priority to U.S. Provisional Patent Application No. 62/789,604, filed on Jan. 8, 2019, and U.S. Provisional Patent Application No. 62/800,665, filed on Feb. 4, 2019, the entire contents of each of which are incorporated by reference herein.

INTRODUCTION

In lung resection of relatively small nodules, it is becoming common practice to use tools to assist a clinician in localizing the small nodules. Several preoperative and intraoperative techniques are presently being used for nodule localization. One of these techniques utilizes small fiducials that are guided to a position adjacent a lung nodule using medical imaging, such as computed tomography.

SUMMARY

Provided in accordance with the disclosure is a localization tool for localizing a nodule of a patient. The localization tool includes an elongated body portion, a magnetic portion coupled to a distal end portion of the elongated body portion, and an electrocautery element coupled to the elongated body portion and configured to be coupled to a source of energy for delivering energy to tissue.

In aspects, the electrocautery element may include a first electrode.

In some aspects, the first electrode may be disposed along a side of the magnetic portion.

In further aspects, the electrocautery element may include a second electrode spaced from the first electrode.

In other aspects, the localization tool may further include a housing having the magnetic portion and the electrocautery element supported therein.

In aspects, the electrocautery element may have a distal end portion that protrudes distally from the housing.

In some aspects, the magnetic portion may include a magnetic core.

In further aspects, the magnet portion may be an electromagnet including a metal coil wrapped about the magnetic core.

In other aspects, the localization tool may further include a magnetic field sensor disposed adjacent the magnetic portion.

In another aspect of the disclosure, a localization system is provided and includes a magnetic fiducial marker and a localization tool. The localization tool includes a housing, an elongated body portion extending proximally from the housing, a magnetic portion coupled to a distal end portion of the elongated body portion and configured to attract the magnetic fiducial marker, and at least one electrode disposed within the housing and configured to be coupled to a source of energy for delivering energy to tissue.

In some aspects, the at least one electrode may include a first electrode disposed within the housing and a second electrode disposed within the housing and spaced from the first electrode.

In other aspects, each of the first and second electrodes may have a distal end portion protruding distally from the housing.

In further aspects, the localization system may further include a magnetic field sensor attached to the housing and disposed adjacent the magnetic portion.

In yet another aspect of the disclosure, a localization tool for localizing a nodule of a patient is provided and includes a housing defining a cavity therein, an elongated body portion extending proximally from the housing, a magnetic portion disposed within the cavity of the housing and configured to attract a magnetic fiducial marker, and an electrocautery element disposed within the cavity of the housing and configured to be coupled to a source of energy. The electrocautery element is configured to deliver energy to tissue for marking the tissue.

In aspects, the electrocautery element may include first and second electrodes disposed on opposite sides of the magnetic portion and supported within the housing.

In some aspects, each of the first and second electrodes may have a distal end portion that protrudes distally from the housing.

Further details and aspects of exemplary embodiments of the disclosure are described in more detail below with reference to the appended figures.

BRIEF DESCRIPTION OF THE DRAWINGS

Various aspects and features of the disclosure are described hereinbelow with references to the drawings, wherein.

DETAILED DESCRIPTION

Figure 1:
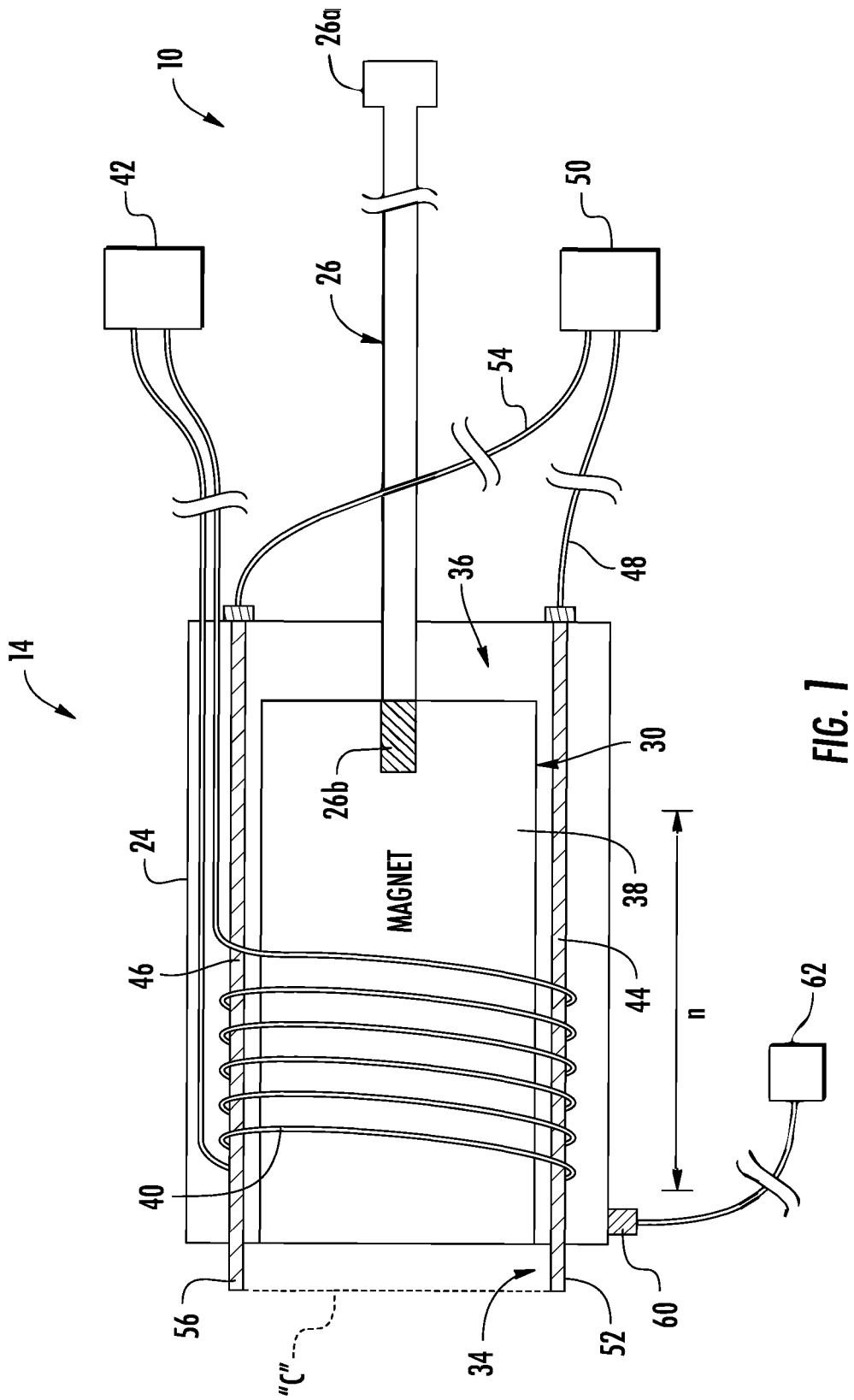
FIG. 1 is a side, cross-sectional view of a localization tool of a localization system.

During some nodule localization procedures, it may be difficult to intraoperatively locate small fiducials without the use of X-ray, digital palpation, and/or a robotic system. As such, there is a continuing need for better and more cost-effective methods for nodule localization.

This disclosure is directed to a localization system for localizing a nodule in a patient, e.g, in a patient's lung. The system includes a magnetic fiducial marker for placing proximate the nodule, and a localization tool for locating the magnetic fiducial marker. The localization tool includes: a handle portion navigable through the chest, lungs, or any other suitable organ; a magnet, such as an electromagnet or a permanent magnet attached to a distal end portion of the handle portion; and an electrocautery element. The electrocautery element may conduct monopolar or bipolar electrosurgical energy for marking tissue surfaces near or at the nodule. During use of the localization system, the magnetic fiducial marker is placed relative to the nodule utilizing X-ray, ultrasound, tomography, or any other suitable imaging system. The localization tool is navigated through the lung to the location of the placed magnetic fiducial marker, whereupon the electrocautery element is activated to mark various surfaces near or at the nodule. This process may be repeated from multiple sides of the nodule until the pleural surface surrounding the outer periphery of the nodule is sufficiently identifiable from the multiple markings. After marking the tissue, the patient can be taken to a surgical suite for the removal of the nodule and the magnetic fiducial marker. In some aspects, tissue marking may occur in the surgical suite. Other types of imaging technology may be utilized, such as computed tomography (CT), magnetic resonance imaging (MRI), fluoroscopy, thermography, ultrasound, optical coherence tomography (OCT), thermal imaging, impedance imaging, laser imaging, or nanotube X-ray imaging. Other navigation techniques may be utilized, including the use of electromagnetic fields, virtual bronchoscopy, AI-enabled navigation, machine learning-enabled navigation, or fiber optic position and shape sensing devices such as Fiber Bragg Gratings, Raleigh scattering, Raman scattering, Brillouin scattering and Fluorescence scattering.

Embodiments of the disclosure will now be described in detail with reference to the drawings in which like reference numerals designate identical or corresponding elements in each of the several views. As is understood in the art, the term "clinician" refers to a doctor, a physician, a nurse, a bronchoscopist, or any other care provider or support personnel. Further, as is understood in the art the term "proximal" refers to the portion of the localization system, or any component thereof, that is closest to the clinician and the term "distal" refers to the portion of the localization system, or any component thereof, that is furthest from the clinician.

FIG. 1 illustrates a localization tool 14 of a localization system 10 configured to locate a magnetic fiducial marker that has been placed relative to a lung nodule, such as, for example, any of the fiducial markers 112, 212, 312, 412, 512, 612 shown in FIGS. 3A-3F.

The localization tool 14 may be reusable with the assistance of a plastic surgical condom (not shown), or may be disposable. The localization tool 14 may be hand-operated or attached to a robotic arm (not shown) and includes a housing 24, an elongated body portion 26 extending proximally from the housing 24, a magnetic portion 30 coupled to a distal end portion 26b of the elongated body portion 26, and an electrocautery element 34. The housing 24 defines a cavity 36 therein and may have a diameter of about 5 mm or less to allow for navigation through the passageways of the lungs or through an incision in the chest. The elongated body portion 26, which in some embodiments may be a flexible rod, has a proximal end portion 26a for grasping by a clinician. The distal end portion 26b of the elongated body portion 26b is fixed to the housing 24.

The magnetic portion 30 of the localization tool 14 is disposed within the cavity 36 of the housing 24. The magnetic portion 30 includes a magnetic core 38 fixed to the distal end portion 26b of the elongated body portion 26. The magnetic core 38 may be made of, coated with, or contain neodymium, iron, or any other suitable magnetic element with strong gauss properties, such that the magnetic portion 30 will be attracted to a magnetic fiducial marker (e.g., fiducial marker 112 of FIG. 3A) from relatively long distances. The magnetic portion 30 of the localization tool 14 is attracted to the bronchoscopically placed magnetic fiducial marker, enabling a precise visualization of the nodule's location for the clinician performing the resection.

The magnetic portion 30, which in some embodiments may be an electromagnet, includes a metal coil 40 wrapped about the magnetic core 38. The metal coil 40 may have any suitable number of turns about the magnetic core 38 and is connected to a power source, such as, for example, a battery 42 for providing a current through the coil 40, thereby generating a magnetic field through the center of the coil 40.

The localization tool 14 includes a magnetic field sensor 60 disposed at any suitable location relative to the magnetic portion 30. For example, the magnetic field sensor 60 may be attached to a distal end portion of the housing 24. The magnetic field sensor 60 may be a MEMS magnetic field sensor, an inductive pickup coil, or any other suitable magnetometer. The magnetic field sensor 60 may be in communication with a computer 62 for communicating a sensed magnetic attraction to a magnetic fiducial marker (e.g., fiducial marker 112 of FIG. 3A). In this way, as the magnetic field sensor 60 is moved closer to a magnetic fiducial marker, the processor of the computer 62 receives a signal that the magnetic portion 30 of the localization tool 14 is approximating the magnetic fiducial marker. The magnetic strength sensed by the magnetic field sensor 60 may be displayed on a display (not shown) of the computer 62. In other aspects of the disclosure, a clinician may determine the proximity between the magnetic portion 30 of the localization tool 14 and the magnetic fiducial marker through a tactile stimulation resulting from interaction between the magnetic portion 30 and the magnetic fiducial marker (e.g., a magnetic pull force, a magnetic attraction, a magnetic repulsion, etc.).

The computer 62 may include a processor (not shown) and a memory (not shown) coupled to the processor. The memory has instructions stored thereon, which are executable by the processor. For example, the instructions may have a correlation between the magnetic strength sensed by the magnetic field sensor 60 and a physical distance between the magnetic field sensor 60 and the magnetic fiducial marker, whereby the processor causes the display to display the determined distance or any suitable indicia representing distance (e.g., a green color indicating proximity and a red color indicating remoteness). The memory may include any non-transitory computer-readable storage media for storing data and/or software that is executable by the processor, e.g., solid-state, volatile, non-volatile, removable, and non-removable.

The electrocautery element 34 of the localization tool 14 includes a first electrode 44 supported in the housing 24 and adjacent the magnetic portion 30. The first electrode 44 has a wire 48 extending proximally therefrom that is electrically connected to a source of electrosurgical energy, such as, for example, an electrosurgical generator 50. The first electrode 44 has a distal end portion 52 protruding distally from the housing 24. In some aspects, the first electrode 44 may be selectively extendible from the housing 24, such that the distal end portion 52 thereof is movable from an extended position to a retracted position, in which the distal end portion 52 is disposed within the cavity 36 of the housing 24. In aspects, the electrocautery element 34 may be a round electrode that surrounds the magnetic portion 30 and is configured to create circular cautery burns on pleura.

In some embodiments, the electrocautery element 34 may include a second electrode 46 for operation of the localization tool 14 in a bipolar mode of operation. The second electrode 46 is supported in the housing 24 on an opposite side of the magnetic portion 30 as the first electrode 44. The second electrode 46 has a wire 54 extending proximally therefrom that is electrically connected to the generator 50. The second electrode 46 has a distal end portion 56 protruding distally from the housing 24. In some aspects, the second electrode 46 may be selectively extendible from the housing 24, such that the distal end portion 56 thereof is movable from an extended position to a retracted position, in which the distal end portion 56 is disposed within the cavity 36 of the housing 24. The coil 40 of the magnetic portion 30 may be wrapped about the first and second electrodes 44, 46.

Figure 2A:
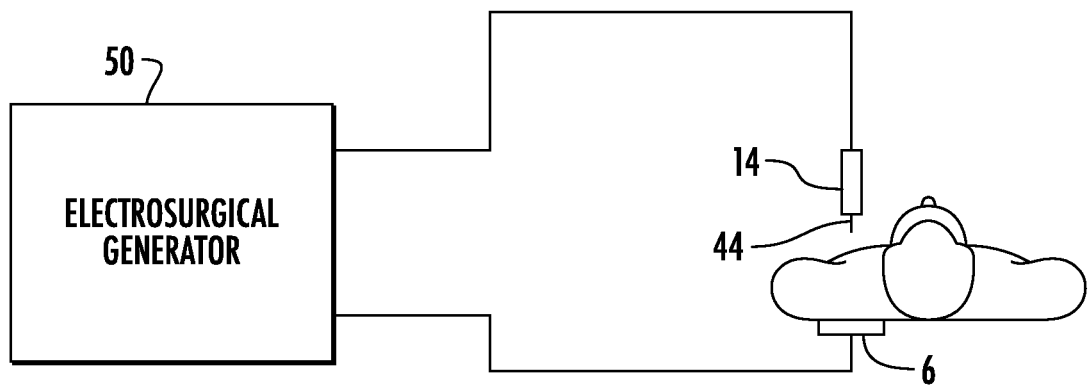
FIG. 2A is a schematic block diagram of an electrosurgical generator and the localization tool of FIG. 1 configured as a monopolar energy delivery instrument.

FIG. 2A shows the localization tool 14 configured to deliver monopolar electrosurgical energy to tissue. In a monopolar mode of operation, the first electrode 44 serves as the source or active electrode that delivers electrosurgical energy from the electrosurgical generator 20 to tissue, and a return electrode 6 serves as a return electrode that carries the current back to the generator 50. The return electrode 6 may be a patient return electrode placed remotely from the active electrode 44 to carry the current back to the generator 50.

Figure 2B:
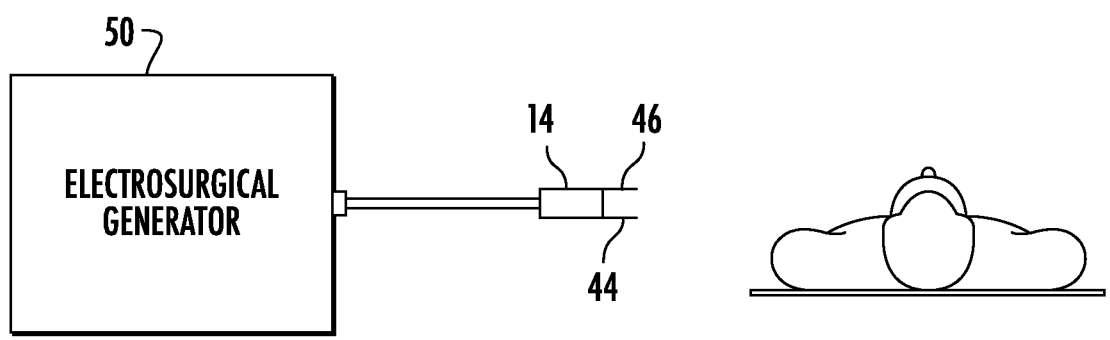
FIG. 2B is a schematic block diagram of an electrosurgical generator and the localization tool of FIG. 1 configured as a bipolar energy delivery instrument.

FIG. 2B shows the localization tool 14 configured to deliver bipolar electrosurgical energy to tissue. In a bipolar mode of operation, one of the first or second electrodes 44 or 46 of the electrocautery element 34 functions as the active electrode for delivering energy to tissue and the other of the first or second electrodes 44 or 46 functions as the return electrode for returning current to the generator 50. The return electrode (e.g., 46) is placed in close proximity to the active electrode (e.g., 44) such that an electrical circuit is formed between the two electrodes, as depicted by the phantom line "C" in FIG. 1.

The generator 50 includes suitable input controls (e.g., buttons, activators, switches, touch screen, etc.) for controlling the generator 50. In addition, the generator 50 may include one or more display screens for providing the user with variety of output information (e.g., intensity settings, treatment complete indicators, etc.). The controls allow the user to adjust power of the electrosurgical energy waveform, as well as the level of maximum arc energy allowed which varies depending on desired tissue effects and other parameters to achieve the desired waveform suitable for a particular task (e.g., tissue blanching, coagulating, tissue sealing, intensity setting, etc.). The localization tool 14 may also include a plurality of input controls that may be redundant with certain input controls of the generator 50.

FIGS. 3A-3F illustrate multiple embodiments of fiducial markers for use with the localization system 10 of FIG. 1. The fiducial markers are shaped in such a way to assist a clinician in determining their direction and/or orientation under radiographic imaging.

Figure 3A:
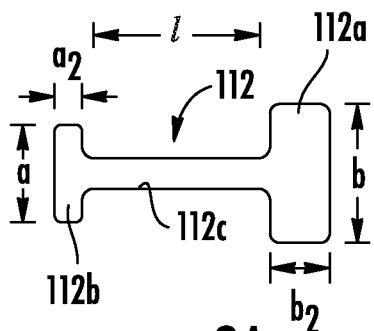
FIGS. 3A-3F are various views of alternate embodiments of fiducial markers of the localization system for use with the localization tool of FIG. 1.

FIG. 3A illustrates a fiducial marker 112 having an asymmetric barbell shape. In particular, the fiducial marker 112 has a first plate 112a having a width and height, a second plate 112b having a width and a height smaller than the first plate 112a, and a bar 112c interconnecting the first and second plates 112a, 112b.

Figure 3D:
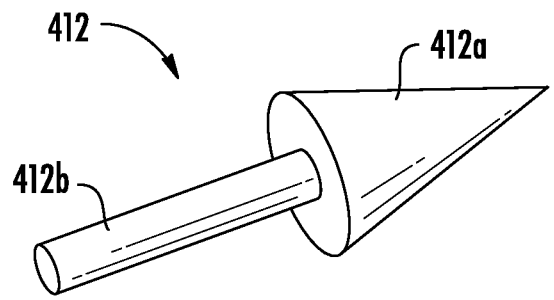
Figure 3B:
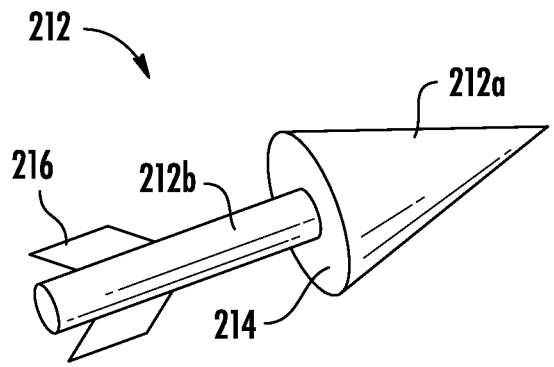

FIG. 3B illustrates a fiducial marker 212 having a cone-shaped head 212a and a rod-shaped tail 212b extending therefrom. A base 214 of the cone-shaped head 212a has a larger diameter than the rod-shaped tail 212b. The rod-shaped tail 212b may have a plurality of fixation elements 218 extending therefrom to facilitate fixation of the fiducial marker 212 in tissue.

Figure 3E:
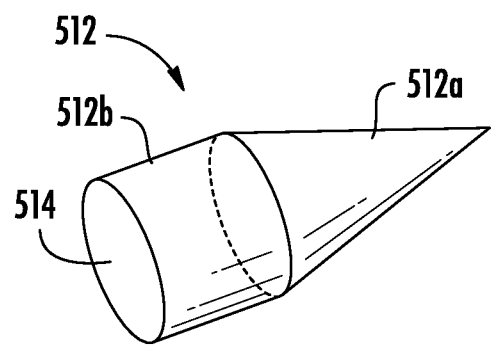
Figure 3C:
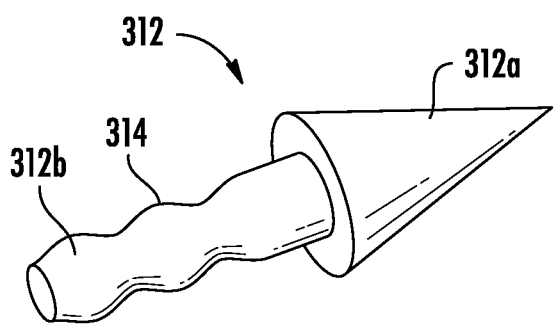

FIG. 3C illustrates a fiducial marker 312 having a cone-shaped head 312a and a rod-shaped tail 312b extending therefrom. The rod-shaped tail 312b has an undulating outer surface 314 defining alternating peaks and troughs along its longitudinal axis. The undulating outer surface 314 is configured to prevent migration of the fiducial marker 312 in tissue.

FIG. 3D illustrates a fiducial marker 412, similar to the fiducial marker 212 shown in FIG. 3B. The fiducial marker 412 has a cone-shaped head 412a and a rod-shaped tail 412b extending therefrom. The rod-shaped tail 412b has a reduced diameter compared to the diameter of the rod-shaped tail 212b of the fiducial marker 212 and may be devoid of fixation elements.

FIG. 3E illustrates a fiducial marker 512 having a cone-shaped head 512a and a cylindrical body portion 512b extending from the cone-shaped head 512a. The cylindrical body portion 512b has a rear surface 514 that may include various configurations (e.g., flat, concave, or convex, etc.).

Figure 3F:
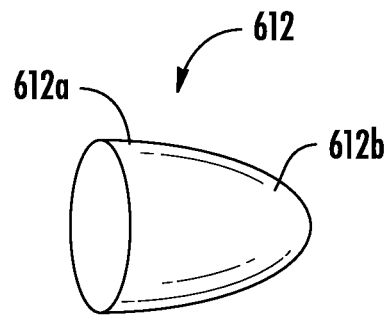

FIG. 3F illustrates a fiducial marker 612 having a generally bullet-like shape configuration that tapers from a first end 612a toward a second end 612b thereof.

The above-described irregular or asymmetrically shaped fiducial markers provide directional information when observed in multi-plane radiography. By providing features that are detectable on radiography or felt during digital palpation, the clinician is given an improved frame of reference, which may minimize the amount of tissue needed to be resected. In aspects, the head portions of any of the fiducial markers described herein may have any suitable shape configured to assist in identifying a direction/orientation of the fiducial marker under radiography. For example, the head portions (e.g., 212a, 312a, 412a, 512a) of the fiducial markers may have a triangular-pyramidal shape, a square-pyramidal shape, or a pyramidal shape having any suitable number of planar faces.

The magnetic fiducial markers may have any suitable fixation elements, such as, for example, wires, barbs, or fletches extending therefrom to limit migration of the magnetic fiducial markers in the airways or parenchymal tissue. The fixation elements may be made from ferrous or non-ferrous materials including plastics, rubbers, metals etc. In certain embodiments, the fixation elements may be fabricated from absorbable material that allows for biological ingrowth to capture the fixation elements. For example, the fixation elements may be fabricated from or coated with poly-glycolic acid (PGA) or bio-scaffold materials like collagen matrices.

The fiducial markers may be made of, coated with, or contain neodymium or any other suitable magnetic element with adequate gauss properties, such that the magnetic fiducial markers can be attracted to other magnetic elements from long distances. Due to the strength of the magnetic properties of the magnetic fiducial markers, the localization tool 14 (FIG. 1) may be able to locate the magnetic fiducial markers through relatively thick tissue planes. The magnetic fiducial markers may also be radiopaque (e.g., the fiducial markers may have a radiopaque coating) so they can be seen in stereotactic body radiation therapy or surgical procedures with imaging systems such as X-ray, cone beam CT, CAT, fluoroscopy, etc. In aspects, the magnetic fiducial markers may include electromagnetic properties and be energized via a power source to enhance the power (gauss) of the magnetic field and/or focus the magnetic field. In aspects, instead of or in addition to making the fiducial markers magnetic, an adhesive coating may be provided having a bond strength selected to lock the localization tool 14 onto the fiducial marker.

In aspects, the fiducial markers may be hollow and configured to store therein a chemical payload to allow for localized identification with, for example, white light, NIR, and/or spectral imaging systems. The chemical payload may include indocyanine green, methylene blue, carmine blue, or fluorophores and may be designed to be released from the fiducial marker at a given rate, all at once, or in the presence of a magnetic field. For example, the fiducial marker may be equipped with a valve configured to selectively release the chemical payload.

In operation, localization of a lung nodule may be performed during pre-operative navigational bronchoscopy using manual or robotic access methods. In some instances, the localization system may be used for percutaneous marking of a tumor under CT or fluoroscopy or intraoperatively using a navigation system or other guidance.

A nodule is located using, for example, x-ray, ultrasound, tomography, or any other suitable imaging system. A delivery tool (not shown), for example, an endobronchial catheter or an endoluminal catheter, preloaded with any of the magnetic fiducial markers 112, 212, 312, 412, 512 or 612, is inserted into a lung of a patient. The delivery tool is guided through the lung to position the magnetic fiducial marker at the location of the nodule. Once in the appropriate position, the magnetic fiducial marker is released from the delivery tool and fixed relative to the nodule.

The elongated body portion 26 of the localization tool 14 is manipulated by the clinician to guide the magnetic portion 30 of the localization tool 14 toward the magnetic fiducial marker. For example, the magnetic portion 30 may be guided toward the magnetic fiducial marker using the magnetic attraction between the magnetic portion 30 and the magnetic fiducial marker and/or utilizing imaging guidance. Upon the magnetic field sensor 60 of the localization tool 14 sensing a magnetic field of the magnetic fiducial marker, which may be indicative of close proximity thereto, the clinician may activate the electrode 44 of the localization tool 14 via an activation switch (not shown) on the localization tool 14, an activation switch (not shown) coupled to the generator 50 (e.g., footswitch), or a user interface (not shown) on the generator 50. The distal end portion 52 of the electrode 44 contacts and delivers electrosurgical energy to a tissue surface (e.g., a lung nodule), thereby marking the tissue surface with a blanched defect. The blanched defect left on the tissue surface is easily identifiable in a variety of conditions, such as in poor lighting or in a bloody environment. In some embodiments, the electrode 44 may be used to mark the tissue surface with a specific shape or pattern to assist in discriminating the superficial defect from natural defects.

After marking the tissue surface, the magnetic portion 30 of the localization tool 14 may be moved to another location around the nodule to mark one or more additional tissue surfaces. The plurality of markings may serve to outline the margin limits of the nodule for the appropriate resection. After sufficiently marking the tissue surface, the patient can be taken to a surgical suite for the removal of the nodule and the magnetic fiducial marker. In aspects, marking the tissue surface may occur while in the surgical suite.

While several embodiments of the disclosure have been shown in the drawings, it is not intended that the disclosure be limited thereto, as it is intended that the disclosure be as broad in scope as the art will allow and that the specification be read likewise. For example, while described with respect to localizing a nodule in a lung, it should be understood that the presently described localization system may be used to locate and mark nodules in other parts of a patient's body. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A localization tool for localizing a nodule of a patient, comprising:
    a housing;
    an elongated body portion having a proximal end disposed proximal to the housing and a distal end terminating within the housing;
    a magnetic core disposed within the housing and coupled to the distal end of the elongated body portion, the magnetic core configured to attract a magnetic fiducial associated with a position of the nodule;
    an electrocautery element coupled to the elongated body portion and disposed within the housing, the electrocautery element configured to be coupled to a source of energy for delivering energy to tissue to mark the tissue;
    a metal coil wrapped around the electrocautery element and the magnetic core, the metal coil configured to generate a magnetic field; and
    a magnetic field sensor attached to the housing and configured to sense a magnetic attraction of the magnetic fiducial to the magnetic core, wherein the magnetic field sensor is in communication with a processor configured to determine a distance between the magnetic field sensor and the magnetic fiducial marker based on the sensed magnetic attraction for display of the determined distance on a display device.

2. The localization tool according to claim 1, wherein the electrocautery element includes a first electrode.

3. The localization tool according to claim 2, wherein the first electrode is disposed along a side of the magnetic core.

4. The localization tool according to claim 2, wherein the electrocautery element includes a second electrode spaced from the first electrode.

5. The localization tool according to claim 1, wherein the electrocautery element has a distal end portion that protrudes distally from the housing.

6. The localization tool according to claim 1, further comprising a magnetic field sensor disposed adjacent to the magnetic core and the metal coil.

7. A localization system, comprising:
    a magnetic fiducial;
    a localization tool including:
        a housing;
        an elongated body portion extending proximally from the housing and having a distal end terminating within the housing;
        a magnetic core disposed within the housing, the magnetic core coupled to the distal end of the elongated body portion and configured to attract the magnetic fiducial associated with a position of a nodule of a patient;
        at least one electrode disposed within the housing and configured to be coupled to a source of energy for delivering energy to tissue to mark the tissue;
        a metal coil wrapped around the at least one electrode and the magnetic core, the metal coil configured to generate a magnetic field; and
        a magnetic field sensor attached to the housing and configured to sense a magnetic attraction of the magnetic fiducial to the magnetic core;
    a processor configured to determine a distance between the magnetic field sensor and the magnetic fiducial marker based on the sensed magnetic attraction; and
    a display configured to display the determined distance.

8. The localization system according to claim 7, wherein the at least one electrode includes a first electrode disposed within the housing and a second electrode disposed within the housing and spaced from the first electrode.

9. The localization system according to claim 8, wherein each of the first and second electrodes has a distal end portion protruding distally from the housing.

10. The localization system according to claim 7, further comprising a magnetic field sensor attached to the housing and disposed adjacent to the magnetic core and the metal coil.

11. A localization tool for localizing a nodule of a patient, comprising:

a housing defining a cavity therein;

an elongated body portion extending proximally from the housing and having a distal end terminating within the housing;

a magnetic core disposed within the cavity of the housing and configured to attract a magnetic fiducial associated with a position of the nodule;

an electrocautery element disposed within the cavity of the housing and configured to be coupled to a source of energy, the electrocautery element configured to deliver energy to tissue for marking the tissue;

a metal coil wrapped around the electrocautery element and the magnetic core, the metal coil configured to generate a magnetic field; and a magnetic field sensor attached to the housing configured to sense the magnetic attraction to the magnetic fiducial, wherein the magnetic field sensor is in communication with a processor configured to determine a distance between the magnetic field sensor and the magnetic fiducial marker based on the sensed magnetic attraction for display of the determined distance on a display device.

12. The localization tool according to claim 11, wherein the electrocautery element includes first and second electrodes disposed on opposite sides of the magnetic core.

13. The localization tool according to claim 12, wherein each of the first and second electrodes has a distal end portion that protrudes distally from the housing.

\* \* \* \* \*